US00PP34608P2

(12) United States Plant Patent
Bisschop et al.

(10) Patent No.: US PP34,608 P2
(45) Date of Patent: Sep. 20, 2022

(54) ***DELPHINIUM* PLANT NAMED 'ET DLP 827'**

(50) Latin Name: ***Delphinium elatum* X (*Delphinium* x *belladonna*)**
Varietal Denomination: ET DLP 827

(71) Applicants: Elisabeth Bisschop, Boijl (NL); Bart Noordhuis, Boijl (NL)

(72) Inventors: Elisabeth Bisschop, Boijl (NL); Bart Noordhuis, Boijl (NL)

(73) Assignee: ETERNAL PLANT BOIJL B.V., Boijl (NL)

( * ) Notice: Subject to any disclaimer, the term of this patent is extended or adjusted under 35 U.S.C. 154(b) by 0 days.

(21) Appl. No.: 17/671,301

(22) Filed: Feb. 14, 2022

(51) Int. Cl.
*A01H 5/02* (2018.01)
*A01H 6/72* (2018.01)

(52) U.S. Cl.
USPC ..... Plt./423
CPC ..... *A01H 6/72* (2018.05)

(58) Field of Classification Search
USPC ..... Plt./423
CPC ..... A01H 6/72; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Delphinium* plant named 'ET DLP 827', characterized by its relatively compact, upright and sturdy plant habit; relatively short internodes; dark green-colored leaves; freely flowering habit; moderately strong to strong flowering stems with dense inflorescences with numerous light purple-colored flowers; and good garden performance.

2 Drawing Sheets

Figure 1:
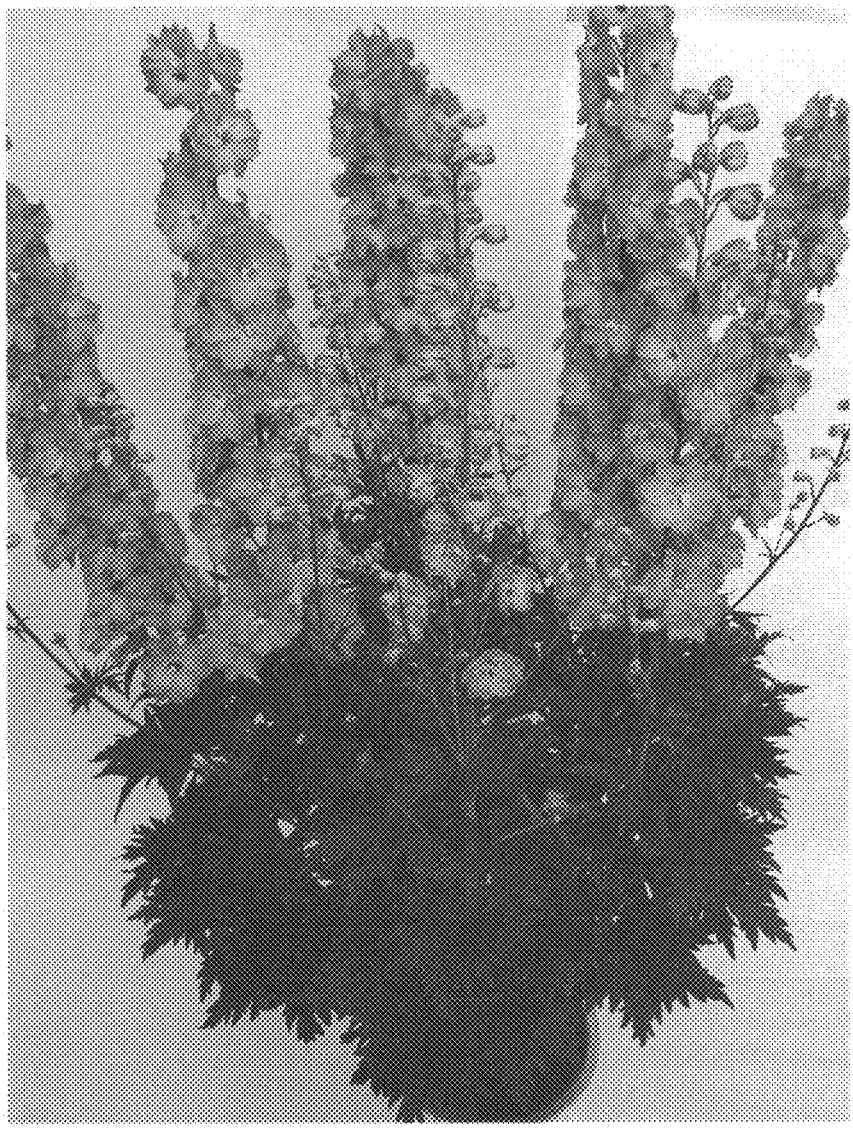

Botanical designation: *Delphinium elatum* X (*Delphinium* x *belladonna*).
Cultivar denomination: 'ET DLP 827'.

CROSS-REFERENCED TO A RELATED APPLICATION & STATEMENT REGARDING PRIOR DISCLOSURES BY INVENTORS/APPLICANTS

This application claims priority to a European Community Plant Breeders' Rights application filed on Oct. 1, 2021, application number 2021/2438. There have been no offers for sale anywhere in the world prior to the effective filing date of this Application and no accessibility to one of ordinary skill in the art could have been derived from the printed Plant Breeder's Rights documents.

The Inventors/Applicants assert that no publications nor advertisements relating to sales, offers for sale or public distribution occurred more than one year prior to the effective filing date of this application. Any information about the claimed plant would have been obtained from a direct or indirect disclosure from the Inventors/Applicants. Inventors/Applicants claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Delphinium* plant, botanically known as *Delphinium elatum* X (*Delphinium* x *belladonna*), typically grown as a perennial garden plant and hereinafter referred to by the name 'ET DLP 827'.

The new *Delphinium* plant is a product of a planned breeding program conducted by the Inventors in Boijl, The Netherlands. The objective of the breeding program is to create new strong and freely-flowering *Delphinium* plants with dense inflorescences and unique and attractive flower colors.

The new *Delphinium* plant originated from a cross-pollination in July, 2014 of a proprietary selection of *Delphinium elatum* identified as code number 1014, not patented, as the female, or seed, parent with a proprietary selection of *Delphinium* x *belladonna* identified as code number 85-D, not patented, as the male, or pollen, parent. The new *Delphinium* plant was discovered and selected by the Inventors as a single flowering plant from within the progeny of the stated cross-pollination in a controlled greenhouse environment in Boijl, The Netherlands in July, 2016.

Asexual reproduction of the new *Delphinium* plant by in vitro meristem culture in a controlled environment in Boijl, The Netherlands, since August, 2017 has shown that the unique features of this new *Delphinium* plant are stable and reproduced true to type in successive generations.

SUMMARY OF THE INVENTION

Plants of the new *Delphinium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'ET DLP 827'. These characteristics in combination distinguish 'ET DLP 827' as a new and distinct *Delphinium* plant:

1. Relatively compact, upright and sturdy plant habit.
2. Relatively short internodes.
3. Dark green-colored leaves.
4. Freely flowering habit.

5. Moderately strong to strong flowering stems with dense inflorescences with numerous light purple-colored flowers.
6. Good garden performance.

Plants of the new *Delphinium* differ primarily from plants of the female parent selection in the following characteristics:

1. Plants of the new *Delphinium* are more compact and shorter than plants of the female parent selection.
2. Flowers of plants of the new *Delphinium* are light purple in color whereas flowers of plants of the female parent selection are pink in color.

Plants of the new *Delphinium* differ primarily from plants of the male parent selection in the following characteristics:

1. Plants of the new *Delphinium* are taller than plants of the male parent selection.
2. Plants of the new *Delphinium* have larger flowers than plants of the male parent selection.

Plants of the new *Delphinium* can be compared to plants of *Delphinium elatum* X (*Delphinium belladona*) 'ET DLP 17-10', disclosed in U.S. Plant Pat. No. 32,993. In side-by-side comparisons, plants of the new *Delphinium* differ primarily from plants of 'ET DLP 17-10' in the following characteristics:

1. Plants of the new *Delphinium* are taller than plants of 'ET DLP 17-10'.
2. Plants of the new *Delphinium* have slightly larger flowers than plants of 'ET DLP 17-10'.
3. Flowers of plants of the new *Delphinium* are light purple in color whereas flowers of plants of 'ET DLP 17-10' are purple violet in color.

Plants of the new *Delphinium* can be compared to plants of *Delphinium elatum* 'Flamingo Star', not patented. In side-by-side comparisons, plants of the new *Delphinium* differ primarily from plants of 'Flamingo Star' in the following characteristics:

1. Plants of the new *Delphinium* are more compact than plants of 'Flamingo Star'.
2. Plants of the new *Delphinium* have stronger flowering stems than plants of 'Flamingo Star'.
3. Flowering stems of plants of the new *Delphinium* are branching whereas flowering stems of plants of 'Flamingo Star' are not branching.
4. Flowers of plants of the new *Delphinium* are light purple in color whereas flowers of plants of 'Flamingo Star' are pink in color.

BRIEF DESCRIPTION OF THE PHOTOGRAPHS

The accompanying colored photographs illustrate the overall appearance of the *Delphinium* plant showing the colors as true as it is reasonably possible to obtain in colored reproductions of this type. Colors in the photographs may differ slightly from the color values cited in the detailed botanical description which accurately describe the actual colors of the new *Delphinium* plant.

The photograph on the first sheet (FIG. 1) comprises a side perspective view of a typical flowering plant of 'ET DLP 827' grown in an container.

Figure 2:
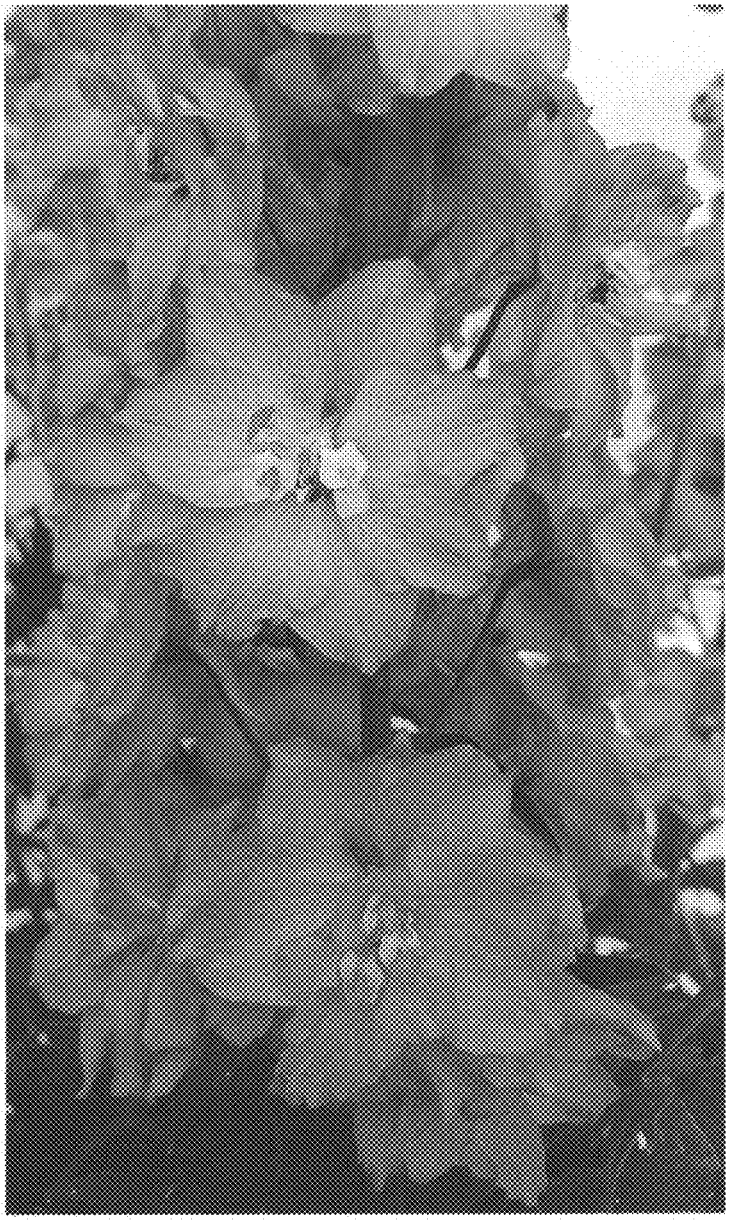

The photograph on the second sheet (FIG. 2) is a close-up view of a typical inflorescence of 'ET DLP 827'.

DETAILED BOTANICAL DESCRIPTION

Plants used for the following description were grown in 21-cm containers during the spring and summer in an outdoor nursery in Boijl, The Netherlands and under cultural practices typical of commercial *Delphinium* production. During the production of the plants, day temperatures ranged from 18° C. to 22° C. and night temperatures ranged from 10° C. to 16° C. Plants were one year old when the photographs and the description were taken. In the following description, color references are made to The Royal Horticultural Society Colour Chart, 2001 Edition, except where general terms of ordinary dictionary significance are used.

Botanical classification: *Delphinium elatum* X (*Delphinium* x *belladonna*) 'ET DLP 827'.

Parentage:

*Female, or seed, parent*.—Proprietary selection of *Delphinium elatum* identified as code number 1014, not patented.

*Male, or pollen, parent*.—Proprietary selection of *Delphinium* x *belladonna* identified as code number 85-D, not patented.

Propagation:

*Type of propagation*.—In vitro meristem culture.

*Time to initiate roots, summer*.—About 12 to 16 days at temperatures ranging from 15° C. to 21° C.

*Time to initiate roots, winter*.—About 15 to 25 days at temperatures ranging from 5° C. to 10° C.

*Time to produce a rooted young plant, summer*.—About four weeks at temperatures ranging from 18° C. to 21° C.

*Time to produce a rooted young plant, winter*.—About five to six weeks at temperatures ranging from 12° C. to 15° C.

*Root description*.—Medium in thickness, fibrous; typically yellowish in color, actual color of the roots is dependent on substrate composition, water quality, fertilizer type and formulation, substrate temperature and physiological age of roots.

*Rooting habit*.—Freely branching; medium density.

Plant description:

*Plant type*.—Herbaceous perennial.

*Plant and growth habit*.—Relatively compact, upright and sturdy plant habit; moderately vigorous to vigorous growth habit and moderate growth rate; freely branching habit.

*Plant height, soil level to top of foliar plane*.—About 50 cm to 55 cm.

*Plant height, soil level to top of floral plane*.—About 100 cm.

*Plant width*.—About 55 cm to 60 cm.

*Internode length*.—About 1 cm to 5 cm.

*Stem strength*.—Moderately strong to strong.

*Stem texture and luster*.—Slightly pubescent; semi-glossy to matte.

*Stem color*.—Close to 143C.

Leaf description:

*Arrangement*.—Single, alternate or slightly whorled towards the plant base.

*Leaf length*.—About 9 cm.

*Leaf width*.—About 15 cm to 16 cm.

*Shape*.—Palmately lobed with three to five lobes per leaf; overall leaf shape, roughly ovate.

*Apex*.—Acute.

*Base*.—Cordate.

*Margin*.—Entire and incised; lobes are shallow to moderate and divergent.

*Texture and luster, upper surface*.—Smooth, glabrous; matte.

*Texture and luster, lower surface*.—Slightly pubescent; rough and rugose; matte

*Venation pattern*.—Palmate.

*Color*.—Developing and fully expanded leaves, upper surface: Close to 137A; venation, close to 144C. Developing and fully expanded leaves, lower surface: Close to 138B; venation, close to 144C.

*Petioles*.—Length: About 3 cm to 10 cm. Diameter: About 2 mm to 5 mm. Strength: Moderately strong to strong. Texture and luster, upper and lower surfaces: Smooth, glabrous; semi-glossy to matte. Color, upper and lower surfaces: Close to 143C.

Flower description:

*Flower arrangement and shape*.—Double star-shaped flowers arranged on dense terminal racemes; flowers face mostly outwardly.

*Flowering habit*.—Freely flowering habit with about 40 flowers developing per inflorescence and more than 500 flowers per plant.

*Fragrance*.—None detected.

*Natural flowering season*.—Long flowering period; plants flower continuously during the spring and summer in The Netherlands.

*Flower longevity*.—Flowers last about two to three weeks on the plant; flowers not persistent.

*Flower buds*.—Length: About 1 cm to 1.5 cm. Diameter: About 1 cm. Shape: Oblong. Texture and luster: Smooth, glabrous; semi-glossy to matte. Color: Close to 142A.

*Inflorescence height*.—About 35 cm to 45 cm.

*Inflorescence diameter*.—About 10 cm.

*Flower diameter*.—About 6 cm to 7 cm.

*Flower height*.—About 2 cm.

*Petals*.—Quantity and arrangement: About ten to twelve petals in whorls; petals imbricate. Length: About 3 cm. Width: About 2.5 cm. Shape: Roughly obovate to elliptic. Apex: Acute to obtuse. Base: Attenuate. Margin: Entire; slightly to moderately undulate. Texture and luster, upper and lower surfaces: Smooth, glabrous; satiny; matte. Color: When opening, upper surface: Close to 76C; towards the margins, close to 77C; central petals, close to 155A and at their center, close to 154C. When opening, lower surface: Close to 76C; towards the margins, close to 77C. Fully opened, upper surface: Close to 77B; towards the margins, close to 77A; central petals, close to 155A and at their center, close to 154C; venation, close to 76A. Fully opened, lower surface: Close to 77C; towards the margins, close to 77A; venation, close to 76A.

*Petaloids*.—Quantity and arrangement: About three to five petaloids in a single whorl; petaloids imbricate. Length: About 3 cm. Width: About 1.5 cm to 2 cm. Shape: Roughly obovate to elliptic. Apex: Acute. Base: Truncate. Margin: Entire; slightly undulate. Texture and luster, upper and lower surfaces: Smooth, glabrous; satiny; matte. Color: When opening, upper surface: Close to 76C; towards the margins, close to 77C. When opening, lower surface: Close to 76C; towards the margins, close to 77C; stripe, close to 142A. Fully opened, upper and lower surfaces: Close to 77C; towards the margins, close to 77A; at the apex, close to 143A; venation, close to 76A.

*Peduncles*.—Length: About 95 cm to 100 cm. Diameter: About 1 cm to 2 cm. Aspect: Erect. Strength: Strong. Texture and luster: Smooth, glabrous; matte. Color: Close to 143C.

*Pedicels*.—Length: About 1.5 cm to 6 cm. Diameter: About 2 mm to 5 mm. Aspect: About 45° from peduncle axis. Strength: Moderately strong. Texture and luster: Smooth, glabrous; matte. Color: Close to 143A.

*Reproductive organs*.—Stamens: Quantity per flower: About 25 to 30. Filament length: About 2 mm to 5 mm. Filament color: Close to 155D. Anther shape: Oblong. Anther length: About 1 mm to 2 mm. Anther color: Close to N199B. Pollen amount: Abundant. Pollen color: Close to N199B. Pistils: Quantity per flower: Four to six. Pistil length: About 6 mm to 12 mm. Stigma diameter: About 1 mm to 3 mm. Stigma shape: Rounded. Stigma color: Close to 76D. Style length: About 5 mm to 8 mm. Style color: Close to 76D. Ovary color: Close to 143B.

*Seeds and fruits*.—To date, seed and fruit development have not been observed on plants of the new *Delphinium*.

Pathogen & pest resistance: To date, plants of the new *Delphinium* have not been noted to be resistant to pathogens and pests common to *Delphinium* plants.

Garden performance: Plants of the new *Delphinium* have exhibited good garden performance and to be tolerant to rain, wind and temperatures ranging from −20° C. to 40° C.

It is claimed:

1. A new and distinct *Delphinium* plant named 'ET DLP 827' as illustrated and described.

* * * * *